United States Patent [19]

Knops et al.

[11] 4,200,643

[45] Apr. 29, 1980

[54] COMBATING FUNGI WITH SPIRO DERIVATIVES OF 3-(3,5-DIHALOGENOPHENYL)-OXAZOLIDINE-2,4-DIONES

[75] Inventors: Hans-Joachim Knops, Wuppertal; Hans-Georg Heine, Krefeld; Wilfried Draber, Wuppertal; Wilhelm Brandes, Leichlingen, all of Fed. Rep. of Germany

[73] Assignee: Bayer Aktiengesellschaft, Leverkusen, Fed. Rep. of Germany

[21] Appl. No.: 7,284

[22] Filed: Jan. 29, 1979

[30] Foreign Application Priority Data

Feb. 4, 1978 [DE] Fed. Rep. of Germany ........ 2804824

[51] Int. Cl.$^2$ ........................ A01N 9/22; C07D 263/52

[52] U.S. Cl. .................................... 424/272; 562/505; 562/506; 260/465 H; 260/557 R; 548/216

[58] Field of Search ........................ 260/307 A, 307 B; 424/272

[56] References Cited

U.S. PATENT DOCUMENTS

| | | | |
|---|---|---|---|
| 3,565,905 | 2/1971 | Maillard | 260/307 FA |
| 3,574,742 | 4/1971 | Lapidus et al. | 260/307 B |
| 3,671,535 | 6/1972 | Faidutti et al. | 260/307 B |

*Primary Examiner*—Alton D. Rollins
*Assistant Examiner*—James H. Turnipseed
*Attorney, Agent, or Firm*—Sprung, Felfe, Horn, Lynch & Kramer

[57] ABSTRACT

Spiro derivatives of 3-(3,5-dihalogenophenyl)-oxazolidine-2,4-diones of the formula

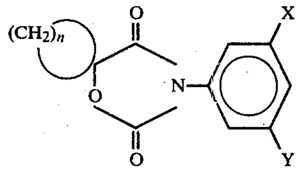

in which X and Y each independently is halogen, and n is 2 or 3, which possess fungicidal properties.

11 Claims, No Drawings

COMBATING FUNGI WITH SPIRO DERIVATIVES OF 3-(3,5-DIHALOGENOPHENYL)-OXAZOLIDINE-2,4-DIONES

The present invention relates to and has for its objects the provision of particular new spiro derivatives of 3-(3,5-dihalogenophenyl)-oxazolidine-2,4-diones which possess fungicidal properties, active compositions in the form of mixtures of such compounds with solid and liquid dispersible carrier vehicles, and methods for producing such compounds and for using such compounds in a new way especially for combating fungi, with other and further objects becoming apparent from a study of the within specification and accompanying examples.

It has already been disclosed that N-(3,5-dihalogenophenyl)-imides, for example N-(3,5-dichlorophenyl)-1,2-dimethylcyclopropane-1,2-dicarboximide, are good agents for combating fungal diseases of plants (see DT-OS (German Published Specification) 2,012,656). It is likewise known that thiuram disulphides, for example tetramethyl-thiuram disulphide, have good fungicidal properties (see U.S. Pat. No. 1,972,961). However, the action of both classes of substances is not always completely satisfactory in certain fields of indication, especially when low amounts and concentrations are applied.

The present invention now provides, as new compounds the spiro derivatives of 3-(3,5-dihalogenophenyl)-oxazolidine-2,4-diones, of the general formula

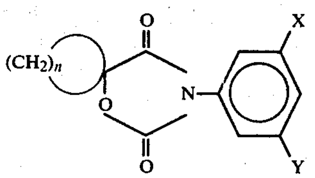

(I), in which

X and Y, which may be identical or different, each represent halogen (in particular fluorine, chlorine, bromine or iodine) and n represents the integer 2 or 3.

Surprisingly, the spiro derivatives, according to the invention, of 3-(3,5-dihalogenophenyl)-oxazolidine-2,4-diones exhibit a considerably higher fungicidal action, especially against species of Botrytis, than the compounds N-(3,5-dichlorophenyl)-1,2-dimethylcyclopropane1,2-dicarboximide and tetramethyl-thiuram disulphide, which are known from the state of the art and are recognised as good agents of the same type of action. The active compounds according to the invention thus represent an enrichment of the art.

The invention also provides a process for the production of a spiro derivative of a 3-(3,5-dihalogenophenyl)-oxazolidine-2,4-dione, of the formula (I), in which an α-hydroxycycloalkylcarboxylic acid (or ester) of the general formula

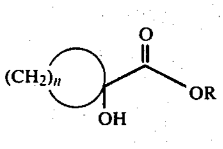

(II), in which

R represents hydrogen or alkyl with 1 to 4 carbon atoms (especially methyl or ethyl) and n has the meaning stated above, (a) is reacted with an isocyanate of the general formula

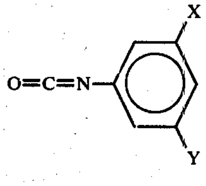

(III), in which

X and Y have the meanings stated above, optionally in the presence of a base and in the presence of a diluent, or (b) is reacted with an aniline of the general formula

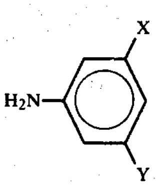

(IV), in which

X and Y have the meanings stated above, in the presence of a diluent and the α-hydroxy-cycloalkylcarboxylic acid amide formed, of the general formula

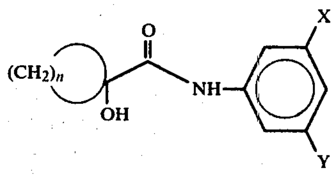

(V), in which

X, Y and n have the meanings stated above, is cyclized with phosgene in the presence of a base.

If α-hydroxy-cyclopropanecarboxylic acid and 3,5-dichlorophenyl isocyanate are used as starting materials in process variant (a), the course of the reaction can be represented by the equation which follows:

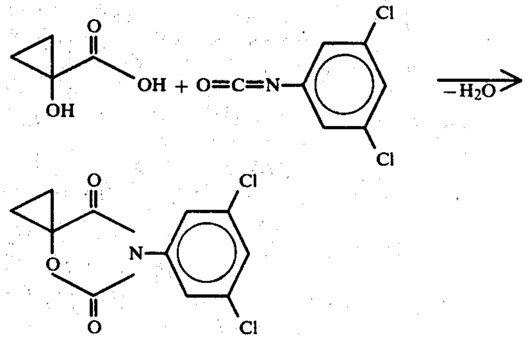

If α-hydroxy-cyclobutanecarboxylic acid ethyl ester and 3,5-dibromophenyl isocyanate are used as starting materials in process variant (a), the course of the reaction can be represented by the equation which follows:

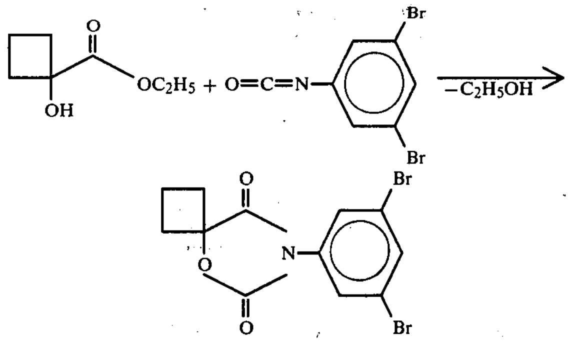

If α-hydroxy-cyclopropanecarboxylic acid, 3,5-dichloroaniline and phosgene are used as starting materials in process variant (b), the course of the reaction can be represented by the equation which follows:

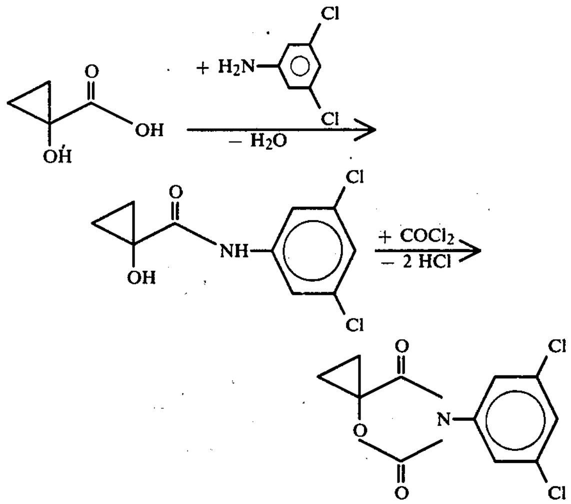

The starting materials of the formula (II) are known (see Liebigs Ann. Chem. 1976, 463 and Chem. Ber. 55, 2738 (1922)). Examples which may be mentioned are: α-hydroxy-cyclopropanecarboxylic acid, α-hydroxy-cyclobutanecarboxylic acid, α-hydroxy-cyclopropanecarboxylic acid methyl ester and ethyl ester and α-hydroxy-cyclobutanecarboxylic acid methyl ester and ethyl ester.

α-Hydroxy-cyclopropanecarboxylic acid can be prepared, for example, by a procedure in which 1,2-bis-(trimethylsiloxy)-1-cyclobutene is first prepared by acyloin condensation of the succinic acid ester in the presence of trimethylchlorosilane, the resulting compound is then brominated, 1-hydroxy-cyclopropanecarboxylic acid being obtained by this route via 1,2-cyclobutanedione by ring contraction. 1-Hydroxy-cyclobutanecarboxylic acid can be prepared, for example, by brominating cyclobutanecarboxylic acid and then treating the resulting 1-bromo compound with an aqueous solution of potassium carbonate.

The starting materials of the formulae (III) and (IV) are generally known compounds of organic chemistry.

Preferred diluents for the reaction in process variant (a) are inert organic solvents, especially aromatic hydrocarbons, for example benzene, toluene, xylene or 1,2-dichlorobenzene, and aliphatic, halogenated hydrocarbons, for example methylene chloride, chloroform or carbon tetrachloride.

If the reaction in process variant (a) is carried out in the presence of a base, all the organic and inorganic bases which can customarily be used can be employed, especially tertiary amines, for example triethylamine or pyridine, and alcoholates, for example potassium tert.-butylate or sodium tert.-butylate.

The reaction temperatures can be varied within a substantial range in process variant (a). In general, the reaction is carried out at from 20° to 100° C., preferably at the boiling point of the particular solvent.

Equimolar amounts of the reactants are preferably used for carrying out process variant (a) according to the invention. If a base is used, this is employed in an equimolar amount when α-hydroxycycloalkanecarboxylic acids are used as starting materials and only in a catalytic amount when α-hydroxycycloalkanecarboxylic acid esters are employed. In order to isolate the compounds of the formula (I), the solvent is distilled off and the residue is worked up by customary methods.

Preferred diluents for the reaction in process variant (b) are inert organic solvents, especially the solvents already mentioned for process variant (a).

Preferred bases for the reaction in process variant (b) are the reagents already mentioned for variant (a).

The reaction temperatures can be varied within a substantial range in process variant (b). In general, the reaction is carried out at from 20° to 100° C., preferably at the boiling point of the solvent used.

Equimolar amounts are preferably used for carrying out process variant (b). The α-hydroxy-cycloalkylcarboxylic acid amides of the formula (V), occurring as the intermediate products, can be reacted directly without isolation. In order to isolate the compounds of the formula (I), the solvent is distilled off and the residue is worked up by customary methods.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens. They develop a particularly good activity against parasitic fungi on above-ground parts of plants.

As plant protection agents, the active compounds according to the invention can be used with particularly good success for combating species of Botrytis, for example against the causative organism of grey mold on strawberries or grapes (*Botrytis cinerea*).

As plant protection agents, the compounds according to the invention can be used for the treatment of soil, for the treatment of seed and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surfaceactive agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.1 to 0.00001 percent by weight, preferably from 0.05 to 0.0001 percent.

In the treatment of seed, amounts of active compound of 0.001 to 50 g, especially 0.01 to 10 g, are generally required per kilogram of seed.

For the treatment of soil, amounts of active compound of 1 to 1000 g, especially 10 to 200 g, are generally required per cubic meter of soil.

The present invention also provides a fungicidal composition containing as active ingredient a compound of the present invention in admixture with a solid or liquefied gaseous diluent or carrier or in admixture with a liquid diluent or carrier containing a surfaceactive agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative example:

EXAMPLE 1

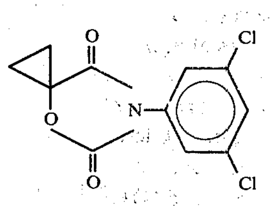

(1)

5.1 g (0.05 mol) of α-hydroxy-cyclopropanecarboxylic acid and 5.05 g (0.05 mol) of triethylamine were dissolved in 200 ml of 1,2-dichlorobenzene at about 100° C. A solution of 9.4 g (0.05 mol) of 3,5-dichlorophenyl isocyanate in 300 ml of 1,2-dichlorobenzene was added dropwise and the mixture was then heated under reflux for 3 hours using a water separator. After the water had been separated off, the mixture was allowed to cool and was concentrated by distilling off the solvent in vacuo. 100 ml of hot ethanol were added to the residue, which was still warm, and the components were mixed thoroughly. During cooling, white crystals separated out, which were filtered off and recrystallized from ethanol. 7 g (51% of theory) of 1-oxa-3-aza-spiro[4,2]heptane-3-(3,5-dichlorophenyl)-2,4-dione of melting point 162° were obtained.

The compounds in Table 1 which follows were obtained in an analogous manner.

Table 1

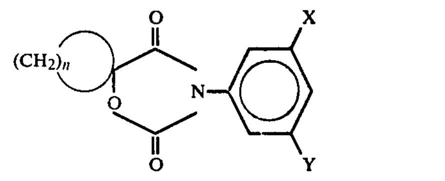

(I)

| Compound No. | n | X | Y |
|---|---|---|---|
| 2 | 3 | Cl | Cl m.p. 148°-50° C. |
| 3 | 3 | Br | Br |
| 4 | 2 | I | I |
| 5 | 2 | Br | Br |
| 6 | 2 | Cl | Br |
| 7 | 3 | Cl | Br |

The fungicidal activity of the compounds of this invention is illustrated by the following example wherein the compound according to the present invention is identified by the number (given in brackets) from Example 1:

EXAMPLE 2

Botrytis test (beans)/protective

Solvent: 4.7 parts by weight of acetone.

Dispersing agent: 0.3 part by weight of alkylaryl polyglycol ether.

Water: 95.0 parts by weight.

The amount of active compound required for the desired concentration of active compound in the spray liquor was mixed with the stated amount of the solvent and the concentrate was diluted with the stated amount of water which contained the stated amount of the dispersing agent.

Plants of *Phaseolus vulgaris* in the 2-leaf stage were sprayed with the spray liquor until dripping wet. After 24 hours, 2 small pieces of agar on which *Botrytis cinerea* had been grown were placed on each leaf. The inoculated plants were set up in a darkened, moist chamber at 20 degrees C. 3 days after the inoculation, the size of the infection spots on the leaves was rated.

In this test, the compound (1) exhibited a good action, which was superior to that of the known compounds N-(3,5-dichlorophenyl)-1,2-dimethyl-cyclopropane-1,2-dicarboximide and tetramethylthiuram disulphide.

It will be appreciated that the instant specification and examples are set forth by way of illustration and not limitation, and that various modifications and changes may be made without departing from the spirit and scope of the present invention.

What is claimed is:

1. A spiro derivative of 3-(3,5-dihalogenophenyl)oxazolidine-2,4-dione of the formula

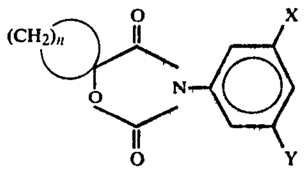

in which

X and Y each independently is halogen, and n is 2 or 3.

2. A compound according to claim 1, wherein such compound is 1-oxa-3-aza-spiro[4,2]-heptane-3-(3,5-dichlorophenyl)-2,4-dione of the formula

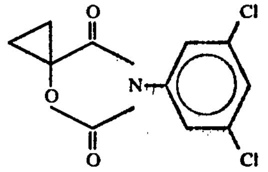

3. A compound according to claim 1, wherein such compound is 1-oxa-3-aza-spiro[4,3]-octane-3-(3,5-dichlorophenyl)-2,4-dione of the formula

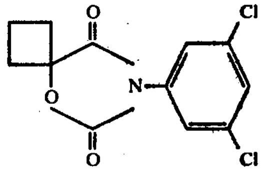

4. A compound according to claim 1, wherein such compound is 1-oxa-3-aza-spiro[4,3]-octane-3-(3,5-dibromophenyl)-2,4-dione of the formula

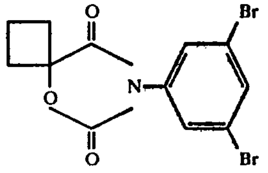

5. A compound according to claim 1, wherein such compound is 1-oxa-3-aza-spiro[4,2]-heptane-3-(3,5-diiodophenyl)-2,4-dione of the formula

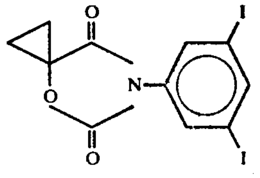

6. A compound according to claim 1, wherein such compound is 1-oxa-3-aza-spiro[4,2]-heptane-3-(3,5-dibromophenyl)-2,4-dione of the formula

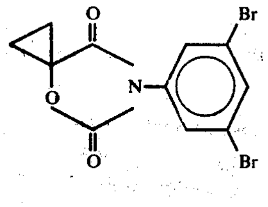

7. A compound according to claim 1, wherein such compound is 1-oxa-3-aza-spiro[4,2]-heptane-3-(3-bromo-5-chlorophenyl)-2,4-dione of the formula

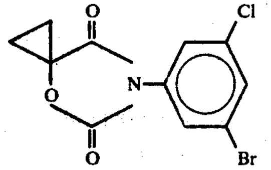

8. A compound according to claim 1, wherein such compound is 1-oxa-3-aza-spiro[4,3]-octane-3-(3-bromo-5-chlorophenyl)-2,4-dione of the formula

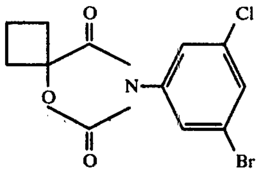

9. A fungicidal composition containing as active ingredient a fungicidally effective amount of a compound according to claim 1 in admixture with a diluent.

10. A method of combating fungi which comprises applying to the fungi, or to a habitat thereof, a fungicidally effective amount of a compound according to claim 1.

11. The method according to claim 10, in which said compound is 1-oxa-3-aza-spiro[4,2]-heptane-3-(3,5-dichlorophenyl)-2,4-dione, 1-oxa-3-aza-spiro[4,3]-octane-3-(3,5-dichlorophenyl)-2,4-dione, 1-oxa-3-aza-spiro[4,3]-octane-3-(3,5-dibromophenyl)-2,4-dione, 1-oxa-3-aza-spiro[4,2]-heptane-3-(3,5-diiodophenyl)-2,4-dione, 1-oxa-3-aza-spiro[4,2]-heptane-3-(3,5-dibromophenyl)-2,4-dione or 1-oxa-3-aza-spiro[4,2]-heptane-3-(3-bromo-5-chlorophenyl)-2,4-dione.

* * * * *